(12) United States Patent
Lee et al.

(10) Patent No.: US 11,246,944 B2
(45) Date of Patent: *Feb. 15, 2022

(54) CERIA NANOCOMPOSITE FOR BIOMEDICAL TREATMENT AND PHARMACEUTICAL COMPOSITION CONTAINING SAME

(71) Applicant: Cenyx Biotech Inc., Seoul (KR)

(72) Inventors: Seung-Hoon Lee, Seoul (KR); Han-Gil Jeong, Seoul (KR); Do Yeon Kim, Seoul (KR); Dong-Wan Kang, Seoul (KR); Jaeyun Kim, Suwon-si (KR); Bong Geun Cha, Seoul (KR)

(73) Assignee: Cenyx Biotech Inc., Seoul (KR)

( * ) Notice: Subject to any disclaimer, the term of this patent is extended or adjusted under 35 U.S.C. 154(b) by 86 days.

This patent is subject to a terminal disclaimer.

(21) Appl. No.: 16/474,049

(22) PCT Filed: Jan. 11, 2017

(86) PCT No.: PCT/KR2017/000353
§ 371 (c)(1),
(2) Date: Jun. 26, 2019

(87) PCT Pub. No.: WO2018/124363
PCT Pub. Date: Jul. 5, 2018

(65) Prior Publication Data
US 2019/0381187 A1    Dec. 19, 2019

(30) Foreign Application Priority Data

Dec. 29, 2016    (KR) .................. 10-2016-0182978
Jan. 4, 2017      (KR) .................. 10-2017-0001312

(51) Int. Cl.
| | | |
|---|---|---|
| A61K 47/60 | (2017.01) | |
| A61K 33/00 | (2006.01) | |
| A61K 47/69 | (2017.01) | |

(52) U.S. Cl.
CPC .......... *A61K 47/6923* (2017.08); *A61K 33/00* (2013.01); *A61K 47/60* (2017.08)

(58) Field of Classification Search
CPC .... A61K 47/6923; A61K 47/60; A61K 33/00; A61K 47/10; A61K 47/6929; A61K 9/14; B82Y 5/00
See application file for complete search history.

(56) References Cited

U.S. PATENT DOCUMENTS

| | | | | |
|---|---|---|---|---|
| 2007/0123996 A1* | 5/2007 | Sugaya | ............... | A61L 27/3847 623/23.51 |
| 2012/0070500 A1* | 3/2012 | Cimini | ............... | A61K 47/6935 424/490 |
| 2014/0271899 A1 | 9/2014 | Leiter et al. | | |
| 2015/0079162 A1* | 3/2015 | Hyeon | ................. | A61K 9/4816 424/451 |
| 2015/0315561 A1* | 11/2015 | Schabbauer | ........... | A61K 38/50 424/94.6 |
| 2019/0240161 A1 | 8/2019 | Lee et al. | | |

FOREIGN PATENT DOCUMENTS

| | | |
|---|---|---|
| KR | 10-2006-0056895 | 5/2006 |
| KR | 20130114469 | 10/2013 |

OTHER PUBLICATIONS

Nguyen, Thanh-Dinh, et al., Nanoscale, Issue 4 (2011) pp. 1-40 (Year: 2011).*
Kim, Tae Ho et al., "Mesoporous Silica-coated Luminescent $Eu^{3+}$ Doped $GdVO_4$ Nanoparticles for Multimodal Imaging and Drug Delivery," *RSC Advances*, 4(86):45687-45695 (Sep. 2014).
Korsvik, Cassandra et al., "Superoxide Dismutase Mimetic Properties Exhibited by Vacancy Engineered Ceria Nanoparticles," *Chemical Communication*, 10(10):1056-1058 (Mar. 2007).
International Search Report and Written Opinion for PCT/KR2017/000353, dated Sep. 12, 2017 (w/English translation of International Search Report).
Yu, Tae Kyung et al., "Aqueous-phase Synthesis of Single-crystal Ceria Nanosheets," *Angewandte Chemie International Edition*, 49(26):4484-4487 (Jun. 2010).
Pirmohamed, Talib et al., "Nanoceria exhibit redox state-dependent catalase mimetic activity," *Chemical Communication*, 46(16):2736-2738(Mar. 2010).
Garcia et al., "Neurological deficit and extent of neuronal necrosis attributable to middle cerebral artery occlusion in rats: statistical validation," *Stroke*, 26(4):627-634 (Apr. 1995).
International Search Report and Written Opinion for PCT/KR2016/011937, dated Jul. 10, 2017.
Kang, Dong-Wan. "Anti-inflammatory Effects of Ceria Nanoparticles in Experimental Intracerebral Hemorrhage Models," The 7th Japanese-Korean Joint Stroke Conference, Scientific Symposium 2 (Oct. 24, 2015).
Kim, Chi Kyung et al., "Anti-inflammatory Effects of Ceria Nanoparticles in Experimental Intracerebral Hemorrhage Models," *Stroke*, 47(Suppl 1), Abstract No. A WP265 (Feb. 2016).
Kim, Chi Kyung et al., "Ceria Nanoparticles that Can Protect against Ischemic Stroke," *Angewandte Chemie International Edition*, 51(44):11039-11043 (Sep. 2012).
Methods in Molecular Biology, vol. 203: In Situ Detection of DNA Damage: Methods and Protocols, Edited by: V. V. Didenko © Humana Press Inc., Totowa, NJ (2002).
Notice of Allowance for Korean Patent Application No. 10-2016-0137505 (dated Sep. 4, 2018) (with machine translation).

(Continued)

*Primary Examiner* — Andrew S Rosenthal
*Assistant Examiner* — Lyndsey M Beckhardt
(74) *Attorney, Agent, or Firm* — Klarquist Sparkman, LLP (57) ABSTRACT

Disclosed are a ceria nanocomposite for biomedical treatment, including a ceria nanoparticle; and a pharmaceutical composition. The disclosed ceria nanocomposite for biomedical treatment includes a ceria nanoparticle and a surface modification layer arranged on the surface of the ceria nanoparticle, wherein the surface modification layer includes a polyethylene glycol residue, and in the ceria nanoparticle, the content of $Ce^{3+}$ is greater than the content of $Ce^{4+}$.

3 Claims, 8 Drawing Sheets

(56) References Cited

OTHER PUBLICATIONS

Office Action for Korean Patent Application No. 10-2016-0137505 (dated Jan. 1, 2018) (with machine translation).
Office Action for Korean Patent Application No. 10-2016-0137505 (dated Jul. 16, 2018) (with machine translation).
Sugawara et al., "A new grading system evaluating bleeding scale in filament perforation subarachnoid hemorrhage rat model," *J Neurosci Methods*, 167(2):327-334 (Jan. 2008).

* cited by examiner

CERIA NANOCOMPOSITE FOR BIOMEDICAL TREATMENT AND PHARMACEUTICAL COMPOSITION CONTAINING SAME

CROSS REFERENCE TO RELATED APPLICATIONS

This is the U.S. National Stage of International Application No. PCT/KR2017/000353, filed Jan. 11, 2017, which in turn claims the benefit of Korean Patent Application No, 10-2016-0182978, filed Dec. 29, 2016 and Korean Patent Application No. 10-2017-0001312, filed Jan. 4, 2017, which applications are incorporated herein in their entireties.

TECHNICAL FIELD

The present disclosure relates to a ceria nanocomposite for biomedical treatment and a pharmaceutical composition including the same. More particularly, the present disclosure relates to a ceria nanocomposite for biomedical treatment, the ceria nanocomposite exhibiting excellent therapeutic effects on inflammatory diseases, and a pharmaceutical composition including the same.

BACKGROUND ART

Biomedical treatment means treatment of inflammatory diseases or other diseases such as infection, bacteremia, sepsis, and systemic inflammatory response syndrome (SIRS) with functional medicine.

Infection refers to a condition in which a pathogenic microorganism has destructive effects on the host organism after invading and proliferating in the host. In establishing an infection, the virulence of a microorganism and host resistance play a crucial role, and so does environmental condition such as climates. Pathogenic microorganism causing the infections include protozoa, bacteria, *Rickettsia*, viruses, fungi, etc.

Routes of infection include direct contact, droplet and its nuclei, food, transdermal transmission, etc. The period between pathogen invasion and clinical onset is called the incubation period, and no specific symptom such as fever is manifested in this period. Generally, the incubation period is several days to several weeks, but some pathogens have varying incubation periods. For example, the incubation period of cholera is tens of hours. It may be several months for tuberculosis and several years or more for leprosy.

Bacteremia refers to a condition in which bacteria enters the systemic blood circulation. In a mild infectious condition, bacteria entering blood circulation are immediately removed by white blood cells and cannot spread to the body. However, when there are excessive amount of bacteria due to a severe infection, they can spread to the body along the blood circulation. This condition is called bacteremia.

For example, in the case of typhoid fever, the typhoid bacilli enter the gastrointestinal tract and proliferates in adjacent lymph nodes. It then enters the blood and spreads throughout the body to create lesions in remote tissue. This process is made via bacteremia. Bacteremia caused by pyogenic bacteria, typhoid, tuberculosis, anthrax, or *brucella* can be fatal.

The most common routes of bacteremia are the genitourinary tract (25%), followed by the respiratory tract (20%), abscess (10%), surgical wound infections (5%), the biliary tract (5%). Other sites consist of 10% and the remaining 25% are uncertain sites.

Bacteremia occurs when bacteria proliferate faster than bacterial clearance by the reticuloendothelial system. Mostly, bacteria enter the blood indirectly through lymphatic vessels from outside the blood vessel. In cases of infective endocarditis, arteriovenous fistula infection, mycotic aneurysm, suppurative phlebitis, and catheter-related infections, bacteria directly enter the blood circulation and spread to the body.

Sepsis refers to "life-threatening organ dysfunction caused by dysregulated host response due to infection". When a local infection by microorganisms occurs, a systemic inflammatory response occurs as a normal protective mechanism in the host, leading to an increase of white blood cells, an increase in vascular permeability, fever, etc. However, in severe infections, these systemic inflammatory responses become abnormally excessive, causing sepsis. If not treated early, sepsis may lead to hypotension due to decrease in effective blood volume, renal dysfunction, and multi-organ failure, ultimately leading to death.

Even in modern medicine, sepsis has high mortality and poor prognosis. The mortality rates of severe sepsis and sepsis shock are serious enough to reach 25%-30% and 40%-70%, respectively. According to data in the United States, 20 billion dollars accounting for 5.2% of total health care spending were annually spent on treating sepsis in 2011.

Despite medical advances such as the development of antibiotics, the reason why we can not overcome sepsis is that antibiotics alone cannot treat sepsis. When sepsis occurs, a series of inflammatory reactions initiated including release of proinflammatory cytokines and reactive oxygen species, which consequently leads to an increase of capillary permeability, electrolyte and acid-base imbalance, and hypotension.

In modern medicine, there is no way to block this inflammatory cascade, except to diagnose sepsis early and to use antibiotics as quickly as possible. Therapeutic agents for suppressing the abnormal inflammatory responses in early sepsis, such as inflammatory cytokine inhibitors or reactive oxygen species scavengers, have not been developed yet. Standard management such as fluid and electrolyte injection or hemodialysis is carried out to prevent organ dysfunction, but this is not a radical method for sepsis pathophysiology, but merely a symptomatic and supportive one.

Systemic inflammatory response syndrome is defined by two or more of the following: higher or lower body temperature than normal, increased pulse rate, increased respiratory rate, and an increase or decrease of white blood cells compared to normal. Although sepsis is the most representative cause of systemic inflammatory response syndrome, it may be caused by many other diseases such as severe trauma, burns, pancreatitis, etc. Since these diseases share many aspects of pathophysiology, effective therapeutic strategy for systemic inflammatory responses is required.

Accordingly, doctors and scientists around the world are making great efforts to decrease mortality from inflammatory diseases. However, there are no therapeutic agents for effectively treating inflammatory diseases while taking into account toxicity or biocompatibility for human.

DESCRIPTION OF EMBODIMENTS

Technical Problem

An aspect of the present disclosure provides a ceria nanocomposite for biomedical treatment, the ceria nanocomposite including ceria nanoparticles.

Another aspect of the present disclosure provides a pharmaceutical composition including the ceria nanocomposite for biomedical treatment.

Solution to Problem

An aspect of the present disclosure provides a ceria nanocomposite for biomedical treatment, the ceria nanocomposite including a ceria nanoparticle and a surface modification layer disposed on the surface of the ceria nanoparticle, wherein the surface modification layer includes a polyethylene glycol residue, and in the ceria nanoparticle, the content of $Ce^{3+}$ is greater than the content of $Ce^{4+}$.

The surface modification layer may include an outer layer including the polyethylene glycol residue and an inner layer of which one end is linked to the ceria nanoparticle and the other end is linked to the polyethylene glycol residue.

The inner layer may include a residue of a multifunctional organic compound, wherein the multifunctional organic compound may have a first terminal group capable of binding to the ceria nanoparticle and a second terminal group capable of binding to a polyethylene glycol derivative which is an origin of the polyethylene glycol residue.

The multifunctional organic compound may include aliphatic aminocarboxylic acid.

The polyethylene glycol derivative may include methoxy PEG succinimidyl glutarate, methoxy PEG succinimidyl valerate, methoxy PEG succinimidyl carbonate, methoxy PEG succinimidyl succinate, methoxy PEG succinimidyl propionate, or a combination thereof.

The ceria nanocomposite may have a particle size of 1 nm to 100 nm.

Another aspect of the present disclosure provides a pharmaceutical composition including the ceria nanocomposite for biomedical treatment.

Advantageous Effects of Disclosure

A ceria nanocomposite for biomedical treatment according to one embodiment of the present disclosure may reduce the mortality and tissue damages caused by inflammatory diseases and may exhibit excellent effects of inhibiting generation of reactive oxygen species and inflammatory responses, thereby being usefully applied in the treatment of inflammatory diseases.

MODE OF DISCLOSURE

Hereinafter, a ceria nanocomposite for biomedical treatment according to one embodiment of the present disclosure will be described in detail.

As used herein, a "residue" refers to an atomic group (a non-reactive atomic group) that remains after any atomic group is eliminated (e.g., a reactive atomic group) in an organic compound.

The ceria nanocomposite for biomedical treatment may be a ceria nanocomposite for treating an inflammatory disease.

The inflammatory disease may include infection, bacteremia, sepsis, systemic inflammatory response syndrome (SIRS), or two or more thereof.

The ceria nanocomposite for biomedical treatment according to one embodiment of the present disclosure may include a ceria ($CeO_2$) nanoparticle and a surface modification layer disposed on the surface of the ceria nanoparticle.

Specifically, the surface modification layer may be disposed to at least partially surround the surface of the ceria nanoparticle. For example, the surface modification layer may consist of one or more substances which are radially arranged at predetermined intervals on the surface of the ceria nanoparticle.

The ceria nanoparticle may have excellent antioxidant and anti-inflammatory effects to play a role in reducing mortality and tissue damages caused by inflammatory diseases.

The surface modification layer may play a role in improving biocompatibility and biosafety of the ceria nanocomposite including the same.

Further the surface modification layer may increase the total size of the ceria nanocomposite to play a role in preventing uptake of the ceria nanocomposite by phagocytes, etc.

Further, the surface modification layer may have a hydrophilic surface to allow the ceria nanocomposite to bind with water in the blood and to prevent the ceria nanocomposite from binding with other ions in the blood when the ceria nanocomposite is injected into the blood, thereby playing a role in preventing aggregation of the ceria nanocomposites and improving colloidal stability of the ceria nanocomposite.

The surface modification layer may include polyethylene glycol residue.

An origin of the polyethylene glycol residue may be a polyethylene glycol derivative. As used herein, the term "polyethylene glycol derivative" refers to a material formed by substituting at least one of hydrogens at both ends of polyethylene glycol with another substituent (e.g., an alkoxy group or a succinimidyl ester group).

The polyethylene glycol derivative may have a weight average molecular weight of about 100 Dalton (Da) to 10,000 Dalton (Da) according to the number of ethylene oxide in a polymer chain.

The polyethylene glycol derivative may include methoxy polyethylene glycol (PEG) succinimidyl glutarate, methoxy PEG succinimidyl valerate, methoxy PEG succinimidyl carbonate, methoxy PEG succinimidyl succinate, methoxy PEG succinimidyl propionate, or a combination thereof. However, the present disclosure is not limited thereto, and the polyethylene glycol derivative may include other various compounds, as long as they may bind with a multifunctional organic compound described below.

In the ceria nanoparticle, the content of $Ce^{3+}$ is greater than the content of $Ce^{4+}$. In ceria nanoparticle, when the content of $Ce^{3+}$ is greater than the content of $Ce^{4+}$, the particle size of the ceria nanocomposite may be decreased, and the antioxidant effect and biocompatibility thereof may be improved.

Further, the surface modification layer may include an outer layer and an inner layer linked to each other.

The outer layer may include the polyethylene glycol residue.

One end of the inner layer may bind to the ceria nanoparticle, and the other end thereof may bind to the polyethylene glycol residue. For example, one end of the inner layer may chemically bind to the ceria nanoparticle, and the other end thereof may also chemically bind (e.g., covalently bind) to the polyethylene glycolresidue.

The inner layer may include a residue of the multifunctional organic compound.

The multifunctional organic compound may have a first terminal group (e.g., a carboxyl group) capable of binding to the ceria nanoparticle and a second terminal group (e.g., an amino group) capable of binding to the polyethylene glycol derivative (specifically, a succinimidyl group) which is an origin of the polyethylene glycol residue. As used herein, the term "multifunctional organic compound" refers to an organic compound having two or more functional groups.

The multifunctional organic compound may include an aliphatic aminocarboxylic acid.

The aliphatic aminocarboxylic acid may include 6-aminohexanoic acid, 5-aminopentanoic acid, 4-aminobutanoic acid, aminocaproic add, aminoundecanoic acid, aminolauric acid, or a combination thereof.

The particle size of the ceria nanocomposite may be 1 nm to 100 nm, e.g., 1 nm to 50 nm, e.g., 1 nm to 5 nm, e.g., 1 nm to 4 nm, or e.g., 2 nm to 3 nm. The size of the ceria nanocomposite is within the range of 1 nm to 100 nm, the ceria nanocomposite may have excellent water dispersibility and biocompatibility. However, as the particle size of the ceria nanocomposite is decreased, water dispersibility and biocompatibility may be improved.

Figure 1:
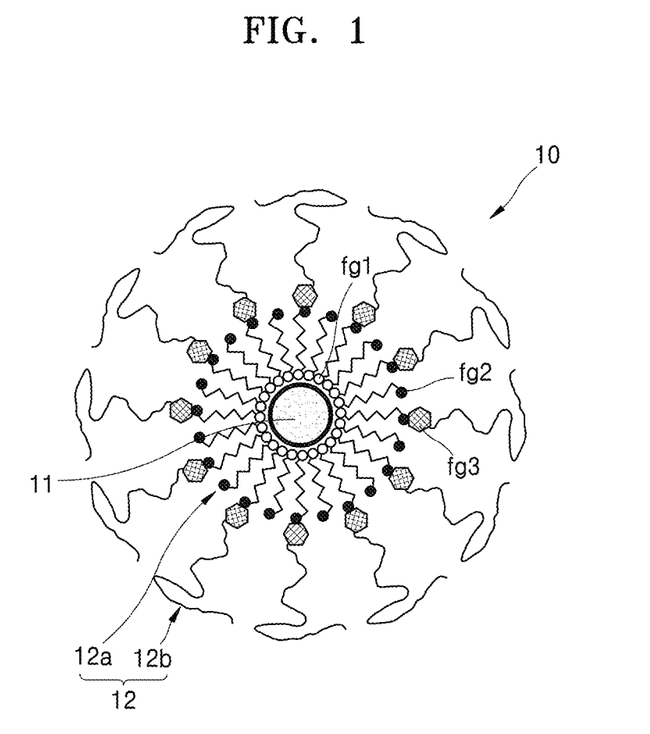
FIG. 1 is a schematic illustration of a ceria nanocomposite according to one embodiment of the present disclosure.

FIG. 1 is a schematic illustration of a ceria nanocomposite 10 according to one embodiment of the present disclosure.

Referring to FIG. 1, the ceria nanocomposite 10 may include a ceria nanoparticle 11 and a surface modification layer 12 disposed on the surface of the ceria nanoparticle.

The surface modification layer 12 includes an inner layer 12a and an outer layer 12b which are linked to each other.

The inner layer 12a may include a multifunctional organic compound residue having a first terminal residue fg1 linked to the ceria nanoparticle 11 and a second terminal residue fg2 linked to the outer layer 12b.

The first terminal residue fg1 may be a carboxylic group (—COOH) or a functional group derived therefrom.

The second terminal residue fg2 may be an amino group (—NH$_2$) or a functional group derived therefrom.

The outer layer 12b may include a polyethylene glycol derivative residue having a third terminal residue fg3 which is linked to the second terminal residue fg2 of the multifunctional organic compound residue included in the inner layer 12a.

The third terminal residue fg3 may be a succinimidyl group or a functional group derived therefrom.

Another embodiment of the present disclosure provides a pharmaceutical composition including the ceria nanocomposite for biomedical treatment.

The pharmaceutical composition may further include a pharmaceutically acceptable additive. The additive may include, for example, a pH adjusting agent, an isotonic agent, a preservative, other excipients, or a combination thereof.

The pH adjusting agent may include sodium hydroxide, potassium hydroxide, sodium hydrogen carbonate, an ammonia solution, potassium citrate, triethanolamine, sodium citrate, or a combination thereof.

The isotonic agent may include D-mannitol, sorbitol, or a combination thereof.

The preservative may include methyl paraoxybenzoate, ethyl paraoxybenzoate, sorbic acid, phenol, cresol, chlorocresol, or a combinations thereof.

An administration route of the ceria nanocomposite for biomedical treatment or the pharmaceutical composition may include intravenous administration, intraarterial administration, intraperitoneal administration, oral administration, intramedullary administration, inhalation administration, intranasal administration, subcutaneous administration, intracerebral administration, intraventricular administration, intrathecal administration, epidural administration, etc.

A daily administration dose of the ceria nanocomposite or the pharmaceutical composition may vary depending on a patient's age, symptoms, a dosage form, etc. For example, the daily administration dose of the ceria nanocomposite or the pharmaceutical composition may be 0.1 mg/kg to 10 mg/kg, for example, 1 mg/kg to 2 mg/kg.

The ceria nanocomposite or the pharmaceutical composition efficiently reaches the cytoplasm through the cell membrane to induce reduction of a water content and a cell death rate at an inflammatory site and the periphery of a bleeding site, thereby exhibiting excellent antioxidant and anti-inflammatory effects. Accordingly, the ceria nanocomposite or the pharmaceutical composition may exhibit effects of improving a survival rate and functional recovery in surviving individuals.

Hereinafter, a method of preparing the ceria nanocomposite for biomedical treatment will be described in detail.

The method of preparing the ceria nanocomposite may include preparing a mixed solution including a cerium precursor, a multifunctional dispersion stabilizer, and a first solvent (S10), heating the mixed solution to prepare a ceria nanoparticle having a surface to which the multifunctional dispersion stabilizer is bound (S20), and mixing the ceria nanoparticle and a polyethylene glycol derivative in a second solvent to bind the multifunctional dispersion stabilizer with the polyethylene glycol derivative, thereby preparing the ceria nanocomposite (S30).

The step S30 may also be referred to as PEGylation of a ceria nanoparticle.

The cerium precursor may include cerium(III) acetate hydrate, cerium(III) acetylacetonate hydrate, cerium(III) carbonate hydrate, cerium(IV) hydroxide, cerium(III) fluoride, cerium(IV) fluoride, cerium(III) chloride, cerium(III) chloride heptahydrate, cerium(III) bromide, cerium(III) iodide, cerium(III) nitrate hexahydrate, cerium(III) oxalate hydrate, cerium(III) sulfate, cerium(III) sulfate hydrate, cerium(IV) sulfate, or a combination thereof.

The multifunctional dispersion stabilizer may be the same as the above-described multifunctional organic compound.

Heating of the mixed solution may be performed at 80° C. to 95° C. for 0.5 minutes to 8 hours.

The steps S10 and S20 may be performed by preparing a cerium precursor solution containing the cerium precursor and the first solvent, preparing a dispersion stabilizer solution containing the multifunctional dispersion stabilizer and the second solvent, heating the dispersion stabilizer solution at 80° C. to 95° C., adding the cerium precursor solution to the heated dispersion stabilizer solution, and then leaving the mixture for 1 minute to 8 hours.

The polyethylene glycol derivative may be the same as the above-described polyethylene glycol derivative.

The first solvent and the second solvent each may be an aqueous solvent. When the first solvent and the second solvent are an aqueous solvent, respectively, the prepared ceria nanocomposite may have little or no toxicity. Thus, when injected into the human body, the ceria nanocomposite may minimize incidence of side effects.

The aqueous solvent may include water, alcohol (e.g., ethanol, methanol, propanol, etc.), or a mixture thereof.

Hereinafter, the present disclosure will be described with reference to the following exemplary embodiments, but the present disclosure is not limited thereto.

EXAMPLE

Example 1: Preparation of Ceria Nanocomposite (Preparation of Ceria Nanoparticle)

6-aminohexanoic acid (1.3117 g, Sigma-Aldrich, St. Louis, USA) was dissolved in deionized water (60 mL), and then heated to 95° C. in air under stirring to prepare a first solution. 37% by weight of HCl (70 µl, Duksan Pure Chemicals, South Korea) was added to the first solution to adjust pH of the first solution to 5.5. Meanwhile, cerium(III) nitrate hexahydrate ($Ce(NO_3)_3 \cdot 6H_2O$, 1.08557 g, Alfa Aeser, Ward Hill, USA) was dissolved in deionized water (50 mL) at room temperature (about 20° C.) to prepare a second solution. Thereafter, the second solution was added to the first solution to prepare a third solution. Thereafter, the third solution was maintained at 95° C. for 1 minute, and then cooled to room temperature (about 20° C.). As a result, ceria nanoparticles having surfaces to which 6-aminohexanoic acid is bound were obtained. The ceria nanoparticles were washed with acetone three times to remove unreacted substances.

(PEGylation of the Ceria Nanoparticle)

20 mg of the prepared ceria nanoparticles was added to 2 mL of deionized water to prepare a suspension. The suspension was mixed with 500 mg of methoxy polyethylene glycol succinimidyl glutarate (a weight average molecular weight: 5,000 Dalton) dissolved in 40 mL of ethanol. This mixture was stirred at room temperature (about 20° C.) for 12 hours to covalently bind the amino group of 6-aminohexanoic acid bound to the surfaces of the ceria nanoparticles and the succinimidyl group of the methoxy polyethylene glycol succinimidyl glutarate. As a result, a ceria nanocomposite having a greater content of $Ce^{3+}$ than $Ce^{4+}$ was obtained.

Comparative Example 1: Preparation of Ceria Nanocomposite (Preparation of Ceria Nanoparticle)

6-aminohexanoic acid (1.3117 g, Sigma-Aldrich, St. Louis, USA) was dissolved in deionized water (60 mL), and then heated to 95° C. in air under stirring to prepare a first solution. 37% by weight of HCl (7 µl, Duksan Pure Chemicals, South Korea) was added to the first solution to adjust pH of the first solution to 6.5. Meanwhile, cerium(III) nitrate hexahydrate($Ce(NO_3)_3 \cdot 6H_2O$, 1.08557 g, Alfa Aeser, Ward Hill, USA) was dissolved in deionized water (50 mL) at room temperature (about 20° C.) to prepare a second solution. Thereafter, the second solution was added to the first solution to prepare a third solution. Thereafter, the third solution was maintained at 95° C. for 8 hours, and then cooled to room temperature (about 20° C.). As a result, ceria nanoparticles having surfaces to which 6-aminohexanoic acid is bound were obtained. Then, the ceria nanoparticles were washed with acetone three times to remove unreacted substances.

(PEGylation of the Ceria Nanoparticle)

20 mg of the prepared ceria nanoparticles was added to 2 mL of deionized water to prepare a suspension. The suspension was mixed with 500 mg of methoxy polyethylene glycol succinimidyl glutarate (a weight average molecular weight: 5,000 Dalton) dissolved in 40 mL of ethanol. This mixture was stirred at room temperature (about 20° C.) for 12 hours to covalently bind the amino group of 6-aminohexanoic acid bound to the surfaces of the ceria nanoparticles and the succinimidyl group of the methoxy polyethylene glycol succinimidyl glutarate. As a result, a ceria nanocomposite having a smaller content of $Ce^{3+}$ than $Ce^{4+}$ was obtained.

Comparative Example 2: Preparation of Ceria Nanocomposite (Preparation of Ceria Nanoparticle)

Cerium(III) nitrate hexahydrate ($Ce(NO_3)_3 \cdot 6H_2O$, 0.5 g, Alfa Aeser, Ward Hill, USA) was dissolved in deionized water (50 mL) at room temperature (about 20° C.) to prepare a cerium solution. Thereafter, 29% by weight of ammonium hydroxide ($NH_4OH$, 50 µl, Sigma-Aldrich, St. Louis, USA) was added to the cerium solution. As a result, crude ceria nanoparticles were obtained. Thereafter, an excessive amount of NaCl (10 g, Samchun, Pyeong-Taek, KOREA) was added to the crude ceria nanoparticles to remove unreacted substances. As a result, purified ceria nanoparticles (hereinafter, referred to simply as "ceria nanoparticles") were obtained.

(PEGylation of the Ceria Nanoparticle)

20 mg of the prepared ceria nanoparticles was added to 2 mL of deionized water to prepare a suspension. The suspension was mixed with 500 mg of methoxy polyethylene glycol succinimidyl glutarate (a weight average molecular weight: 5,000 Dalton) dissolved in 40 mL of ethanol. This mixture was stirred at room temperature (about 20° C.) for 12 hours to perform PEGylation of the ceria nanoparticles.

Evaluation Example

Evaluation Example 1: Analysis of Surface Image

Figure 2:
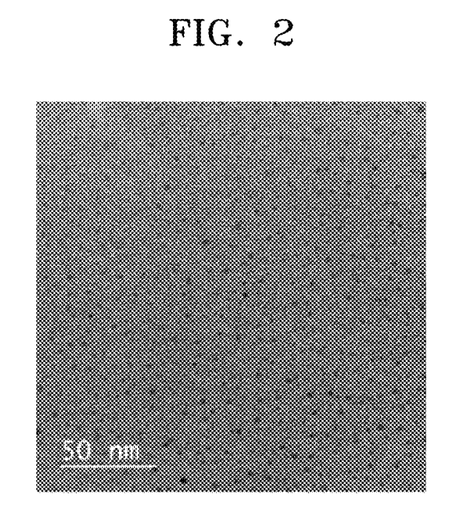
FIG. 2 is a transmission electron microscope (TEM) image of a ceria nanocomposite prepared in Example 1.
Figure 3:
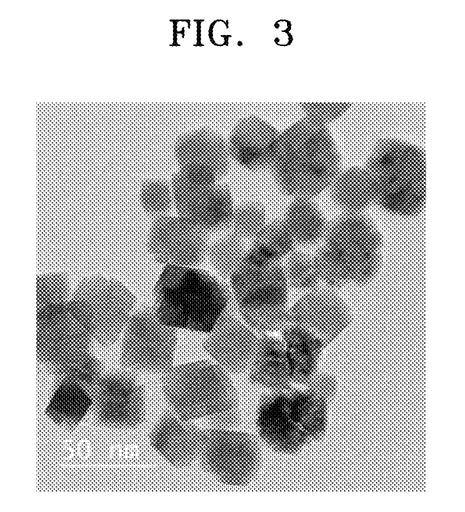
FIG. 3 is a TEM image of a ceria nanocomposite prepared in Comparative Example 1.
Figure 4:
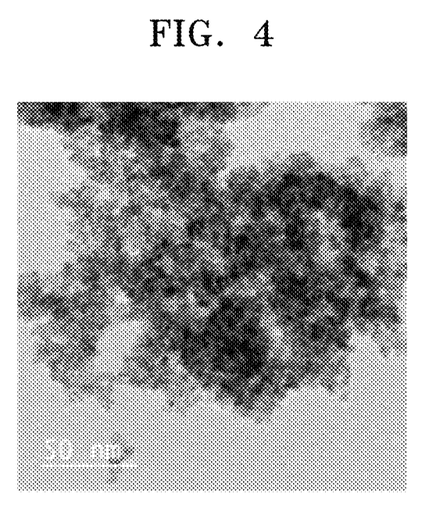
FIG. 4 is a TEM image of a ceria nanocomposite prepared in Comparative Example 2.

Transmission electron microscope (TEM) images of the ceria nanocomposites prepared in Example 1, Comparative Example 1, and Comparative Example 2 were photographed and shown in FIGS. 2 to 4, respectively. FIG. 2 is a TEM image of the ceria nanocomposite prepared in Example 1, FIG. 3 is a TEM image of the ceria nanocomposite prepared in Comparative Example 1, and FIG. 4 is a TEM image of the ceria nanocomposite prepared in Comparative Example 2. TEM instrument used herein was JEM-3010 model of JEOL, Ltd.

Referring to FIG. 2, it was found that the ceria nanocomposite prepared in Example 1 had a small particle size and the particles were separated from each other, indicating excellent dispersibility.

Referring to FIG. 3, it was found that the ceria nanocomposite prepared in Comparative Example 1 had a larger particle size than the ceria nanocomposite prepared in Example 1, suggesting that the ceria nanocomposite prepared in Comparative Example 1 will exhibit lower antioxidant effect and lower biocompatibility than the ceria nanocomposite prepared in Example 1.

Referring to FIG. 4, it was found that the ceria nanocomposite prepared in Comparative Example 2 showed aggregation of ceria nanoparticles before PEGylation, and thus the respective ceria nanoparticles were not PEGylated, but the whole duster of the aggregated ceria nanoparticles was PEGylated, suggesting that the ceria nanocomposite prepared in Comparative Example 2 will exhibit even lower antioxidant effect and lower biocompatibility than the ceria nanocomposite prepared in Comparative Example 1.

Evaluation Example 2: Analysis of Particle Size Distribution

Figure 5:
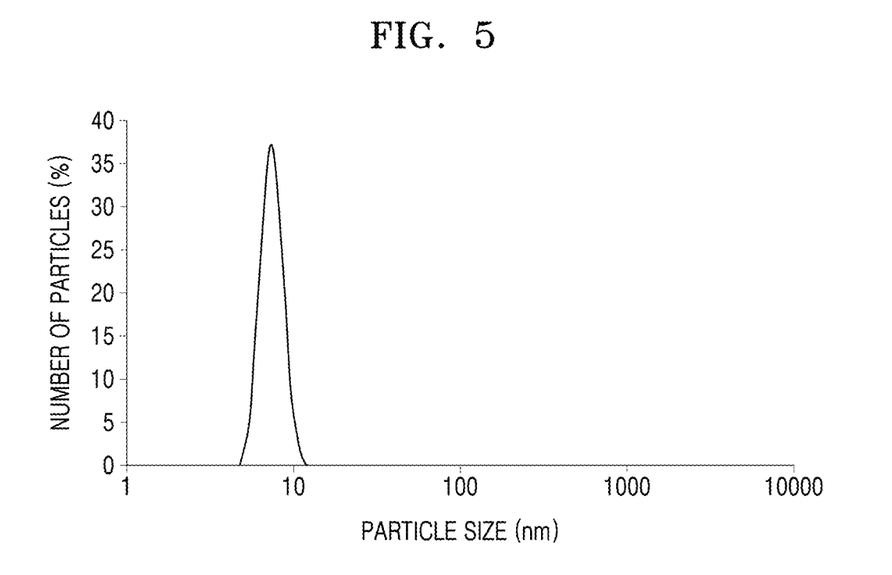
FIG. 5 is a dynamic light scattering (DLS) spectrum of the ceria nanocomposite prepared in Example 1.
Figure 6:
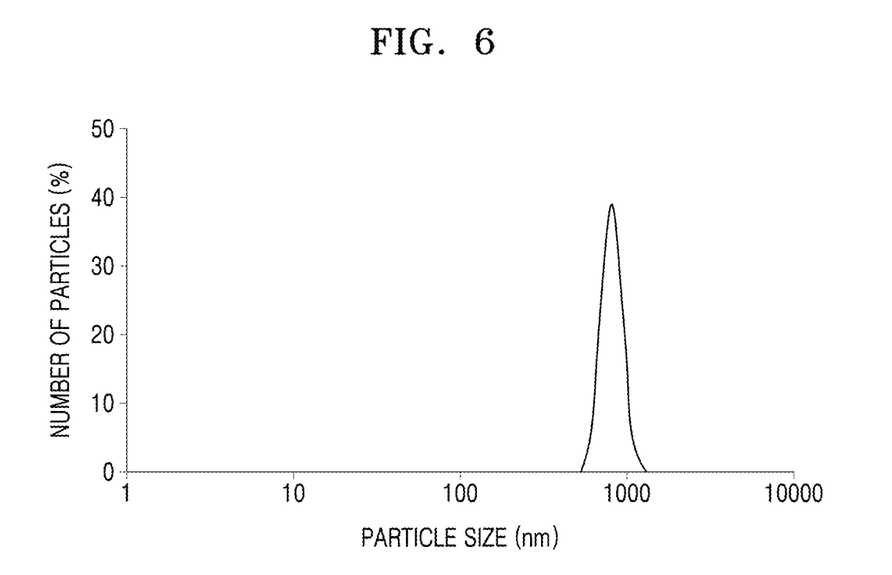
FIG. 6 is a DLS spectrum of the ceria nanocomposite prepared in Comparative Example 2.

Dynamic light scattering (DLS) spectra of the ceria nanocomposites prepared in Example 1 and Comparative Example 2 were analyzed and shown in FIGS. 5 and 6, respectively. FIG. 5 is a DLS spectrum of the ceria nanocomposite prepared in Example 1, and FIG. 6 is a DLS spectrum of the ceria nanocomposite prepared in Comparative Example 2. DLS instrument used herein was Zetasizer Nano ZS model of Malvern.

Referring to FIG. 5, it was found that the ceria nanocomposite prepared in Example 1 had an average particle size of about 10 nm.

Referring to FIG. 6, it was found that the ceria nanocomposite prepared in Comparative Example 2 had an average particle size of about 800 nm.

Evaluation Example 3: Analysis of Oxidation State of Cerium

Figure 7:
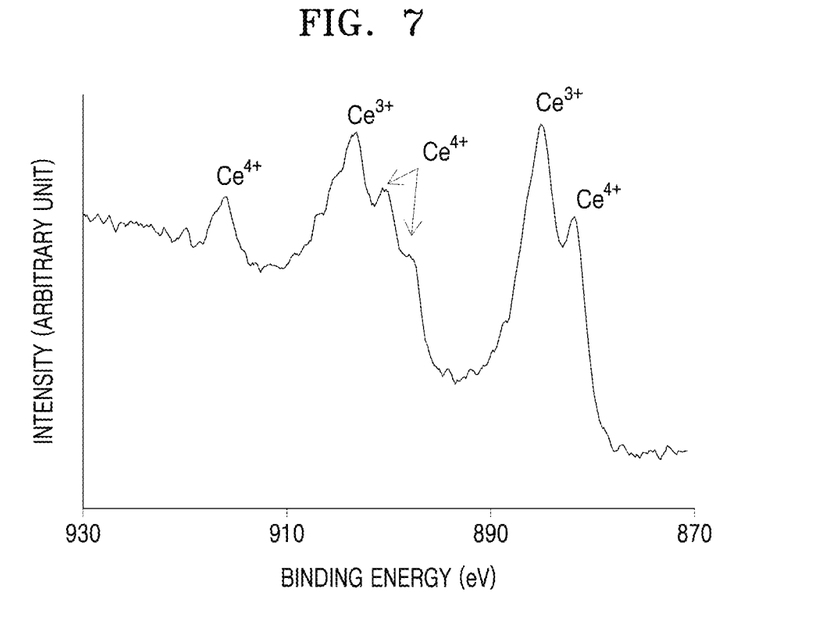
FIG. 7 is an X-ray photoelectron spectroscopy (XPS) spectrum of the ceria nanocomposite prepared in Example 1.
Figure 8:
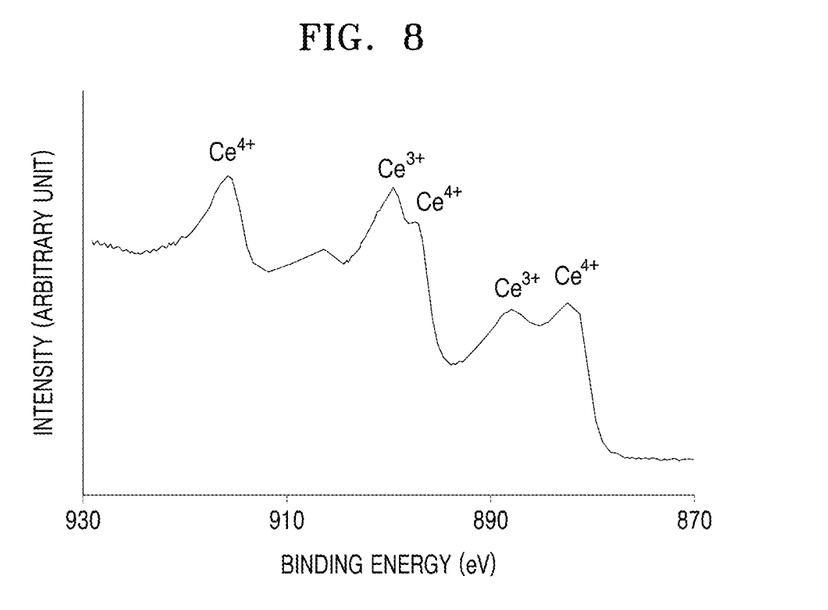
FIG. 8 is an XPS spectrum of the ceria nanocomposite prepared in Comparative Example 1.

X-ray photoelectron spectroscopy (XPS) spectra of the ceria nanocomposite prepared in Example 1 and the ceria nanocomposite prepared in Comparative Example 1 were obtained by XPS, and shown in FIGS. 7 and 8, respectively. FIG. 7 shows an XPS spectrum of the ceria nanocomposite prepared in Example 1, and FIG. 8 shows an XPS spectrum of the ceria nanocomposite prepared in Comparative Example 1. XPS spectrometer used herein was ESCALAB250 model of Thermo Scientific.

Referring to FIG. 7, it was found that the ceria nanocomposite prepared in Example 1 had a greater content of $Ce^{3+}$ (57% by weight) than $Ce^{4+}$ (43% by weight).

Referring to FIG. 8, it was found that the ceria nanocomposite prepared in Comparative Example 1 had a smaller content of $Ce^{3+}$ (25% by weight) than $Ce^{4+}$ (75% by weight).

Evaluation Example 4: Analysis of Antioxidant Effect

Figure 9:
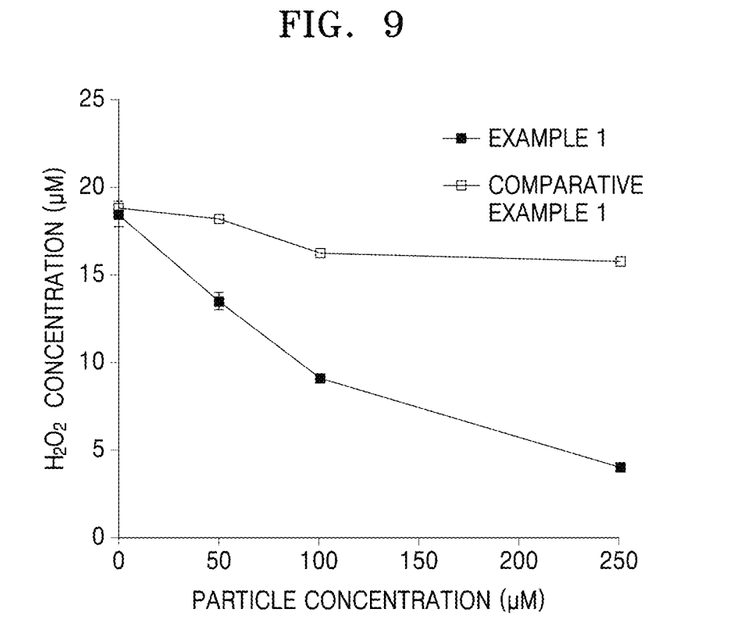
FIG. 9 is a graph showing antioxidant effects according to particle concentrations of the ceria nanocomposite prepared in Example 1 and the ceria nanocomposite prepared in Comparative Example 1.

Antioxidant effects of the ceria nanocomposite prepared in Example 1 and the ceria nanocomposite prepared in Comparative Example 1 were analyzed using an Amplex® Red hydrogen peroxide/peroxidase assay kit (A22188) (Invitrogen detection technologies, USA). In detail, with respect to each of the ceria nanocomposite prepared in Example 1 and the ceria nanocomposite prepared in Comparative Example 1, four kinds of solutions, each having a particle concentration of 0 μM, 50 μM, 100 μM, or 250 μM and a hydrogen peroxide concentration of 20 μM, were prepared. Thereafter, each of the solutions was left under stirring for 1 hour. Thereafter, a concentration of hydrogen peroxide in each solution was measured, and the results are shown in FIG. 9. The concentration of hydrogen peroxide was measured using a fluorescence intensity reader (Thermo Scientific, Varioskan lux).

Referring to FIG. 9, the ceria nanocomposite prepared in Example 1 was found to have excellent antioxidant effect (i.e., $H_2O_2$ scavenging effect), as compared with the ceria nanocomposite prepared in Comparative Example 1.

Evaluation Example 5: ROS Scavenging Effect as Sepsis Therapeutic Effect

Figure 10:
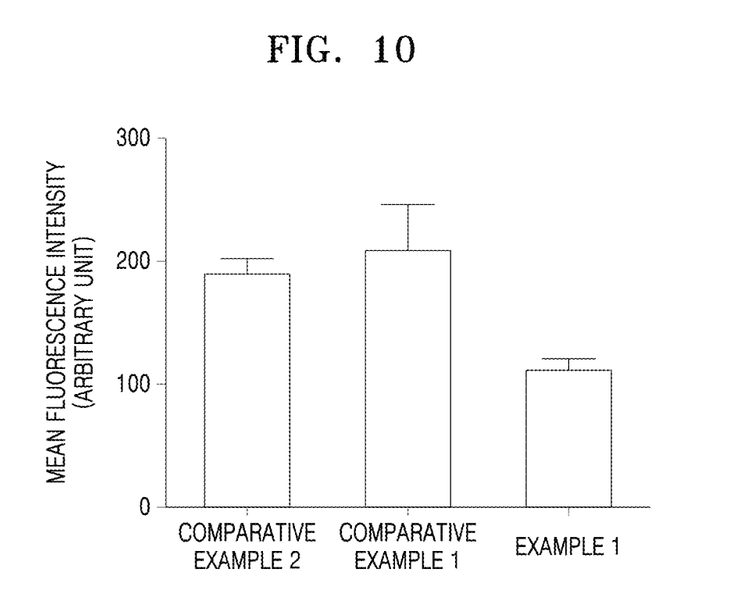
FIG. 10 is a graph showing mean fluorescence intensity (an indicator of reactive oxygen species), which indicates sepsis therapeutic effects of the ceria nanocomposite prepared in Example 1, the ceria nanocomposite prepared in Comparative Example 1, and phosphate buffered saline (PBS) of Comparative Example 2.

Cultured RAW 264.7 cells were washed with phosphate buffered saline (PBS: 137 mM of sodium chloride, 10 mM of phosphate buffer, 2.7 mM of potassium chloride, Amresco, USA) once and suctioned, and seeded in a fresh medium (DMEM, 10% by weight of fetal bovine serum (FBS) added, 1% by weight of penicillin+streptomycin added), and harvested using a scrapper. Thereafter, the cells were seeded in a 6-well plate at a density of $2 \times 10^6$ cells per well. To stimulate the cells, 1 μg/ml of lipopolysaccharide (Sigma-Aldrich, USA) was injected to each well. Simultaneously, the substance described in Table 1 below was diluted with PBS at a concentration of 0.1 mM, and the obtained diluted solution was dispensed into wells, or no substance was dispensed into wells, and the contents of the wells were allowed to react under culture conditions of 37° C. and $CO_2$ for 6 hours. 6 hours later, the medium was removed and washed with cold PBS solution (2 mL) at 4° C. Then, cold PBS solution (2 mL) at 4° C. was dispensed into the washed medium and the cells were separated from the medium by pipetting. The cells were collected in tubes, and centrifuged at 1200 rpm for 3 minutes to obtain a pellet-shaped cell mass. Thereafter, 2',7'-dichlorofluorescein diacetate (DCF-DA) was diluted with warm PBS at 37° C. at a final concentration of 2 μM, and 1 mL thereof was dispensed into each tube to disperse the obtained pellet-shaped cell mass, which was then allowed to react under culture conditions of 37° C. and $CO_2$ for 20 minutes in the dark. Thereafter, centrifugation was performed to obtain a pellet-shaped cell mass, which was then washed once by dispersing in cold PBS solution (2 mL) at 4° C., and centrifuged again to obtain a pellet-shaped cell mass. Finally, propidium iodide (PI, Life technologies) was diluted with cold PBS at 4° C. at a concentration of 3 μM, and 1.5 mL thereof was dispensed into each tube to disperse the obtained pellet-shaped cell mass. Thereafter, to measure the content of reactive oxygen species (ROS), mean fluorescence intensity of 30,000 PI-negative cells (i.e., living cells) was measured using a fluorescence-activated cell sorter (BD-FACSCalibur, BD Biosciences, New Jersey, US), and the results are shown in FIG. 10. To improve reliability of the evaluation results, the experiment was repeated four times for each group, and the mean value thereof was recorded as the mean fluorescence intensity.

Referring to FIG. 10, Example 1 exhibited excellent ROS scavenging effect, as compared with Comparative Examples 1 and 2.

TABLE 1

| | Kind of substance used |
|---|---|
| Example 1 | Ceria nanocomposite prepared in Example 1 |
| Comparative Example 1 | Ceria nanocomposite prepared in Comparative Example 1 |
| Comparative Example 2 | No substance added |

Evaluation Example 6: Tissue Damage- and Inflammation-Reducing Effects of Ceria Nanocomposite as Sepsis Therapeutic Effect <Cecal Ligation and Puncture (CLP) Assay>

All experimental procedures were approved by Institutional Animal Care and Use Committee of Seoul National University. To induce sepsis in 6-week-old male C57BL/6 mice (Koatech), CLP was performed. In detail, C57BL/6 mice were anesthetized with isoflurane, and disinfected with a betaine solution (10% by weight povidone-iodine). Then, skin incision was made to expose the cecum. Then, ligation of the cecum was conducted distal to the ileocecal valve using 6-0 silk, the ligated cecum was punctured with a 26-gauge needle. As a result, feces leaked into the peritoneum, leading to polymicrobial bacteremia and sepsis.

<Drug Administration>

Sepsis-induced tissue damages and degree of inflammation occurrence were evaluated in the following two cases: C57BL/6 mice treated with PBS of Comparative Example 2 and C57BL/6 mice treated with the ceria nanocomposite prepared in Example 1. In the case treated with PBS of Comparative Example 2, after CLP, 300 µl of PBS was administered intraperitoneally. In the case treated with the ceria nanocomposite of Example 1, after CLP, the ceria nanocomposite (2 mg/kg) was administered intraperitoneally.

<Histopathologic Examination>

8 hours after CLP, the cecum, stomach, and liver were removed from each of the C57BL/6 mice. Frozen tissue sections were fixed in 4% by weight of formalin in phosphate buffered saline (PBS) (a product of Amresco, pH 7.1-7.3), and stained with hematoxylin and eosin. Images of the tissue sections were photographed using an optical microscope, and the results are shown in FIG. 11.

Figure 11:
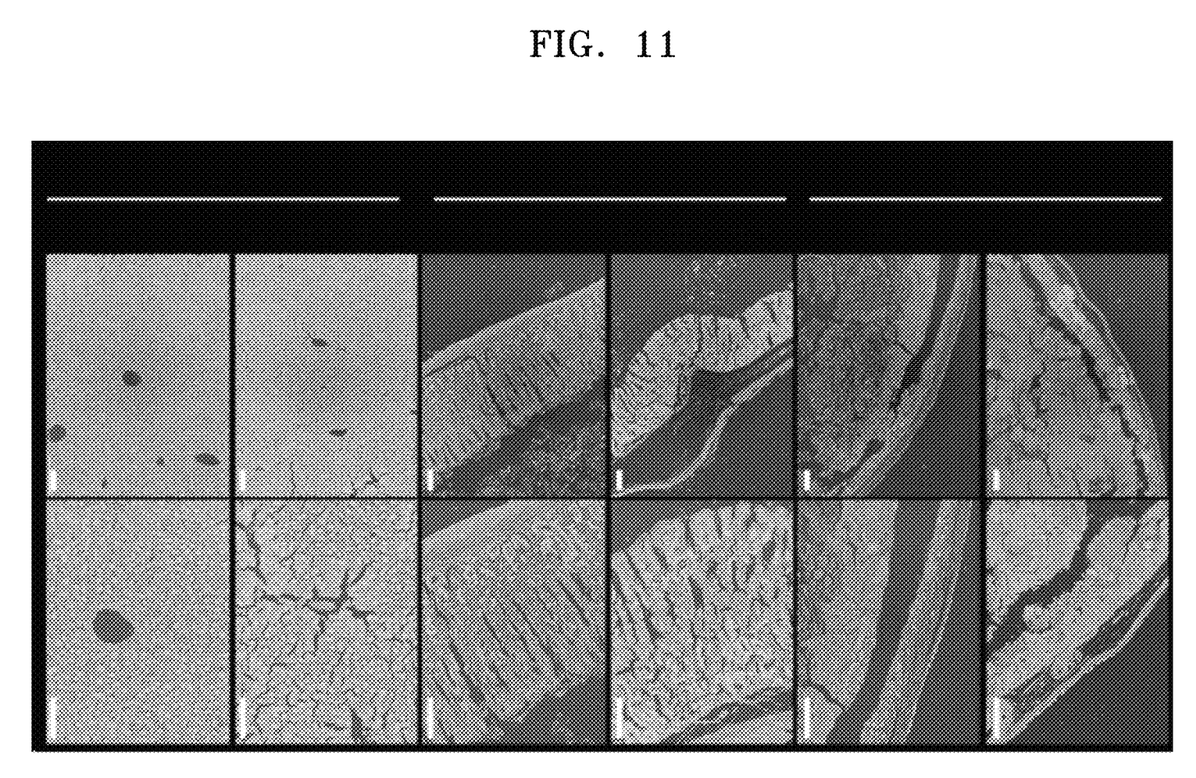
FIG. 11 is an optical microscope image showing tissue damage and the degree of inflammation generation in the liver, stomach, and cecum, which indicates sepsis therapeutic effects of the ceria nanocomposite prepared in Example 1 and PBS of Comparative Example 2.

Referring to FIG. 11, the ceria nanocomposite prepared in Example 1 exhibited the excellent effects of reducing tissue damages and inflammation in the cecum, stomach, and liver, as compared with PBS of Comparative Example 2.

Evaluation Example 7: Survival Rate-Increasing Effect of Ceria Nanocomposite as Sepsis Therapeutic Effect <CLP Assay>

All experimental procedures were approved by Institutional Animal Care and Use Committee of Seoul National University. To induce sepsis in 6-week-old male C57BL/6 mice, CLP was performed. In detail, C57BL/6 mice were anesthetized with isoflurane, and disinfected with a betaine solution (10% by weight povidone-iodine). Then, skin incision was made to expose the cecum. Then, ligation of the cecum was conducted distal to the ileocecal valve using 6-0 silk, the ligated cecum was punctured with a 26-gauge needle. As a result, feces leaked into the peritoneum, leading to polymicrobial bacteremia and sepsis.

<Evaluation of Mortality>

Sepsis-induced mortality was evaluated in the following three groups: eighteen C57BL/6 mice treated with PBS of Comparative Example 2, fifteen C57BL/6 mice treated with the ceria nanocomposite prepared in Example 1, and fifteen C57BL/6 mice treated with imipenem of Comparative Example 3. In the case treated with PBS of Comparative Example 2, after CLP, 300 µl of PBS was administered intraperitoneally. In the case treated with the ceria nanocomposite prepared in Example 1, after CLP, the ceria nanocomposite (2 mg/kg) was administered intraperitoneally. In the case treated with imipenem of Comparative Example 3, after CLP, 500 µg of imipenem (Prepenem®, 530/532 mg imipenem/cilastatin per vial, JW Pharmaceutical, Seoul, Korea) was administered intraperitoneally every 12 hours, before mice died. The C57BL/6 mice were observed for 14 days, and their survival was examined every 24 hours. The results of examining survival rates are shown in FIG. 12.

Figure 12:
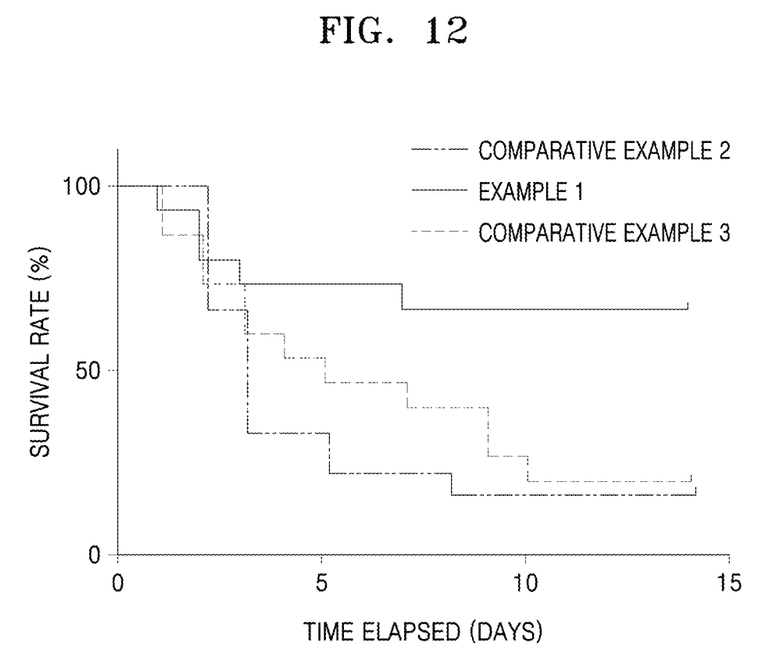
FIG. 12 is a graph showing survival rates indicating sepsis therapeutic effects of the ceria nanocomposite prepared in Example 1, PBS of Comparative Example 2, and imipenem of Comparative Example 3.

Referring to FIG. 12, when the ceria nanocomposite prepared in Example 1 was administered into the C57BL/6 mice, the survival rate was increased, as compared with those of the C57BL/6 mice administered with PBS of Comparative Example 2 and the C57BL/6 mice administered with imipenem of Comparative Example 3. In Example 1, Comparative Example 2, and Comparative Example 3, a plurality of C57BL/6 mice as described above were used in the experiments, and the survival rate was expressed as a mean value thereof.

While the present disclosure has been described with reference to the figures and embodiments, the embodiments are merely examples, and it will be understood by those skilled in the art that various changes in form and other embodiments equivalent thereto may be performed. Therefore, the technical scope of the disclosure is defined by the technical idea of the appended claims.

The invention claimed is:

1. A ceria nanocomposite for biomedical treatment, the ceria nanocomposite comprising a ceria nanoparticle having a surface, and a surface modification layer disposed on the surface of the ceria nanoparticle,
   wherein the surface modification layer comprises a polyethylene glycol residue, and in the ceria nanoparticles, the content of $Ce^{3+}$ is greater than the content of $Ce^{4+}$,
   wherein the surface modification layer comprises an outer layer including the polyethylene glycol residue and an inner layer of which one end is linked to the ceria nanoparticle and the other end is linked to the polyethylene glycol residue,
   wherein the inner layer comprises a residue of a multifunctional organic compound, and the residue of a multifunctional organic compound has a first terminal residue linked to the ceria nanoparticle and a second terminal residue linked to the polyethylene glycol residue of the outer layer,
   wherein the polyethylene glycol residue has a third terminal residue which is linked to the second terminal residue of the residue of a multifunctional organic compound included in the inner layer, wherein the first terminal residue is a carboxylic group (—COOH), the second terminal residue is an amino group (—NH2), and the third terminal residue is a succinimidyl group, wherein there is no other group linked to the polyethylene glycol residue of the outer layer except for the residue of a multifunctional organic compound, wherein the multifunctional organic compound comprises aliphatic aminocarboxylic acid, wherein the polyethylene glycol residue is a residue of methoxy PEG succinimidyl glutarate, methoxy PEG succinimidyk valerate, methoxy PEG succinimidyl carbonate, methoxy PEG succinimidyl succinate, methoxy PEG succinimidyl propionate, or any combination thereof.

2. The ceria nanocomposite for biomedical treatment of claim 1, wherein the ceria nanocomposite has a particle size of 1 nm to 100 nm.

3. A pharmaceutical composition comprising the ceria nanocomposite for biomedical treatment of claim 1.

* * * * *